128/660

United States Patent [19]
Hassler et al.

[11] Patent Number: 4,541,436
[45] Date of Patent: Sep. 17, 1985

[54] ULTRASONIC TOMOGRAPHY DEVICE

[75] Inventors: Dieter Hassler, Uttenreuth; Wolfgang Mittelstaedt, Neunkirchen, both of Fed. Rep. of Germany

[73] Assignee: Siemens Aktiengesellschaft, Berlin and Munich, Fed. Rep. of Germany

[21] Appl. No.: 520,387

[22] Filed: Aug. 4, 1983

[30] Foreign Application Priority Data

Aug. 19, 1982 [DE] Fed. Rep. of Germany ....... 3230897

[51] Int. Cl.⁴ .............................................. A61B 10/00
[52] U.S. Cl. ........................................ 128/660; 73/626
[58] Field of Search .................. 128/660; 73/618–620, 73/626

[56]  References Cited
U.S. PATENT DOCUMENTS

| 4,105,018 | 8/1978 | Greenleaf et al. | 128/2 V |
|---|---|---|---|
| 4,233,988 | 11/1980 | Dick et al. | 128/660 |
| 4,322,974 | 4/1982 | Abele et al. | 128/660 X |
| 4,339,952 | 7/1982 | Foster | 128/660 X |
| 4,362,058 | 12/1982 | Abele | 128/660 X |
| 4,455,872 | 6/1984 | Kossoff et al. | 128/660 X |

OTHER PUBLICATIONS

Resolution & Image Quality by Ultrasonic Echo Tomography: Experimental Approach, by Hundt et al., Siemens AG.
Ultrasonic Reflectivity Tomography: Reconstruction with Circular Transducer Arrays, by Norton & Linzer (1979).

Primary Examiner—Kyle L. Howell
Assistant Examiner—Francis J. Jaworski
Attorney, Agent, or Firm—Mark H. Jay

[57] ABSTRACT

The invention involves an ultrasonic tomography device having an ultrasonic transmitting and receiving system for scanning an object under examination from different angles line by line, a fluid tank for immersing the object to be examined, a cover for the fluid tank with a round opening in the center for inserting the object under examination, and a support for an ultrasonic transmitting and receiving system which rotates in the fluid tank around an essentially vertical axis aligned toward the round opening in the center of the cover. In the case of such ultrasonic tomography devices, there is both the requirement of obtaining information from areas as close to the chest wall as possible, and the necessity of distinguishing localized information that can be traced back to artifacts, from real localized information. For this purpose, the invention provides an additional horizontal axis, intersecting the vertical axis just a few millimeters below the surface of the fluid, which is attached to a second angled support rotating around a vertical axis. From this additional horizontal axis is suspended a revolving, essentially L-shaped support bearing a second ultrasonic transmitting and receiving system on its free end that is capable of revolving through the median perpendicular to the central opening in the cover, and whose direction of radiation is aligned to the mid-point of the central opening in the cover. An ultrasonic tomography device designed in accordance with the invention is particularly suited for use in medical technology.

8 Claims, 4 Drawing Figures

ULTRASONIC TOMOGRAPHY DEVICE

BACKGROUND OF THE INVENTION

The invention relates to an ultrasonic tomography device with an ultrasonic transmitting and receiving system for line-by-line scanning from different angles of an object under examination. The invention includes a fluid tank for immersion of the object to be examined, a cover for the fluid tank with a round opening in the center for insertion of the object under examination, and a support for an ultrasonic transmitting and receiving system which rotates in the fluid tank around an essentially vertical axis aligned in the direction of the round opening in the center of the cover.

Ultrasonic tomography devices can be operated according to both the transmission and the reflection methods. An ultrasonic tomography device for transmission tomography (UCTT), for example, is disclosed by U.S. Pat. No. 4,105,018. Ultrasonic tomography devices for reflection tomography (UCTR), for example, are disclosed by "Resolution and Image Quality by Ultrasonic Echo Tomography: Experimental Approach" by E. Hundt, G. Maderlechner, E. Kronmueller, and E. Trautenberg from the "Fifth International Symposium on Ultrasonic Imaging and Tissue Characterization and Second International Symposium on Ultrasonic Materials Characterization", June 1–6, 1980, page 7. "Ultrasonic Reflectivity Tomography: Reconstruction with Circular Transducer Arrays" by Stephen J. Norton and Melvin Linzer from "Ultrasonic Imaging 1", 1979, pages 154 to 184, also discloses devices for reflection tomography.

In existing ultrasonic tomography devices, the transmitting system can be mounted on a support that can be rotated around a verticle axis, so that horizontal sections known as "coronal sections" can be made from different directions through the object under examination, such as a female breast or male testicle, which is immersed in a fluid tank. The "coronal sections" are created by rotating the support around the vertical axis. In order to record the entire object under examination in this manner, the relative vertical position between the transmitting and the receiving system and the object under examination must be changed after each individual section. This permits only indirect determination of structural changes in the verticle direction by evaluating the information from a minimum of two adjacent sections.

SUMMARY OF THE INVENTION

The object of the invention is an ultrasonic tomography device that makes it possible to gain additional information that provides a graphic representation of three dimensional structural patterns in as clear a form as possible.

Therefore, in an ultrasonic tomography device such as the type already mentioned, an additional horizontal axis which intersects the vertical axis just a few millimeters below the surface of the fluid, is attached to a second angled support rotating around a vertical axis. Suspended from this additional horizontal axis is a rotatable, essentially L-shaped support which carries a second ultrasonic transmitting and receiving system on its free end. This second system which can revolve through the median perpendicular to the opening in the center of the cover, focuses its radiation on the midpoint of the opening in the center of the cover. This arrangement of two transmitting and receiving systems revolving in a fluid tank, allows the intermittent recording of both horizontal or "coronal sections" in different planes, and vertical or "sagittal sections" of the object under examination from a revolving position around the median perpendicular. The "coronal" and "sagittal sections" that pass through the same point on the object under examination not only convey a three-dimensional image of a change in structure at their intersecting points, but also make it possible to check whether objects detected in the other corresponding system are real and not the result of artifacts.

In order to examine a breast as close to the chest wall as possible, the invention can also include a semi-circular gear which surrounds the horizontal axis and is attached to the second angled support revolving around the vertical axis. A motor, attached to the L-shaped support, drives a pinion which engages the gear. This makes it possible to place the horizontal axis, around which the second transmitting and receiving system rotates, directly underneath the contact area for the patient; for example, a few millimeters below the fluid surface, since all structural components required for adjustment can then be accomodated below the level of the horizontal axis. In addition, a gear, in contrast to a lever bar, permits a uniform rotation speed for the second transmitting and receiving system, regardless of the respective rotation position. Finally, this drive mechanism can be housed in the area of the L-shaped support so that only a minimum amount of space is utilized.

The invention can also include a vertical adjustment for the two supports which rotate around the vertical axis. This adjustability makes it possible to record "coronal sections" at different heights without raising or lowering the patient each time.

In another embodiment of the invention the first ultrasonic transmitting and receiving system functions according to the principles of ultrasonic transmission and the associated detector array is attached to the second angled support which rotates around the vertical axis. In this design, the outside perimeter of the detector array of the first transmitting and receiving system can be adapted to fit exactly the free space required for the rotation of the second transmitting and receiving system around the horizontal axis.

Other features and advantages of the invention will be apparent from the following detailed description, and from the claims.

For a full understanding of the present invention, reference should now be made to the following detailed description and to the accompanying drawings.

BRIEF DESCRIPTION OF THE DRAWINGS

FIG. 4 is a schematic diagram of the sound lobes of two ultrasonic transmitters having different diameters.

DETAILED DESCRIPTION

Figure 1:
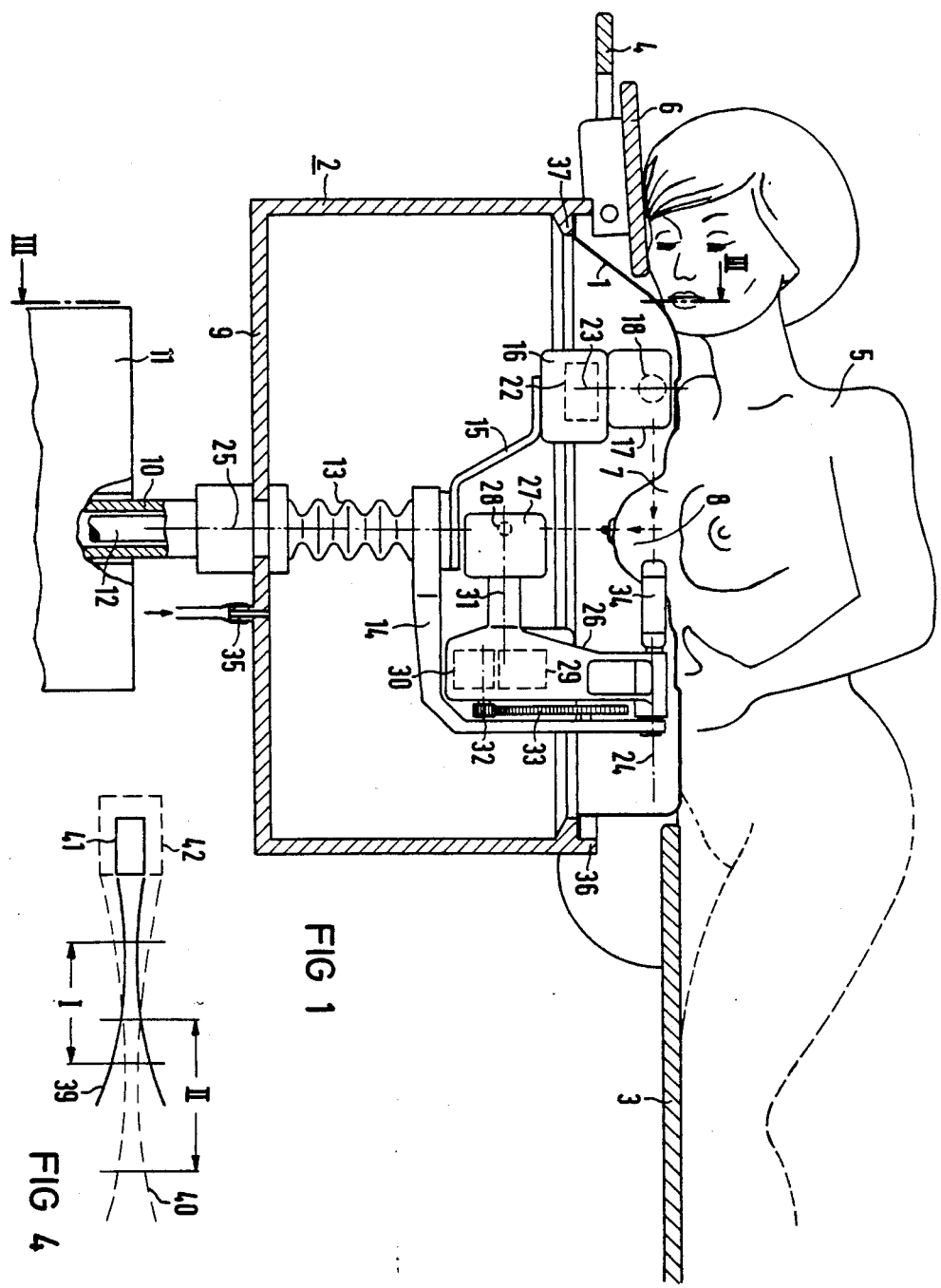
FIG. 1 is a cross-section of an ultrasonic tomography device with a female patient lying on it.

FIG. 1 shows a cross-section of fluid tank 2, with cover 1 in place, and patient support table 3 which has an opening in the area of the cover. Also, on patient support table 3 is head support 6 which can be adjusted to the position of patient 5 by handle 4. The cover has round opening 7 in its center through which the object to be examined 8 can be introduced into the center of the fluid tank. Tubular shaft 10 extends through bottom 9 of fluid tank 2. The shaft is linked to drive mechanism 11 (not shown) which is located under the fluid tank. Inside tubular shaft 10 is another shaft 12 which can not be rotated independently of shaft 10. However, shaft 12 can be moved independent of shaft 10 in its axial direction. This inner shaft 12 is sealed by rubber bellows 13. It is bolted to two support 14, 15 whose free arms angle upwards and extend on opposite sides.

Two waterproof containers 16, 17 are fastened, one above the other, to support 15, as shown in FIG. 1. Upper cylindrical container 17 supports four ultrasonic converters 18, 19, 20, 21 with different diameters, on its barrel, offset by 90 degrees from each other. Motor 22 mounted in lower container 16, permits rotation of upper container 17 around its symmetrical axis 23.

An axle extending along horizontal axis 24 is attached to angled support 14 directly below cover 1 and a few millimeters beneath the surface of the fluid level. This axis is aligned so that its extension intersects vertical axis 25 around which both shafts 10 and 12, and the two angled supports 14 and 15 revolve. Suspended from the axis extending along the horizontal axis 24 is revolving L-shaped support 26 which supports cylindrical container 27 on its free end. This cylindrical container 27 also supports four (only one shown) ultrasonic converters 28 on its perimeter, with each converter being offset by 90 degrees from the other converters. Two motors 29, 30 are mounted on L-shaped support 26. Motor 29 rotates container 27 around its horizontal symmetrical axis 31. The other motor 30 drives pinion 32 which protrudes from the opposite side of L-shaped support 26. This pinion engages a semi-circular gear 33, which is attached to angled support 14 and which curves around horizontal axis 24.

Figure 3:
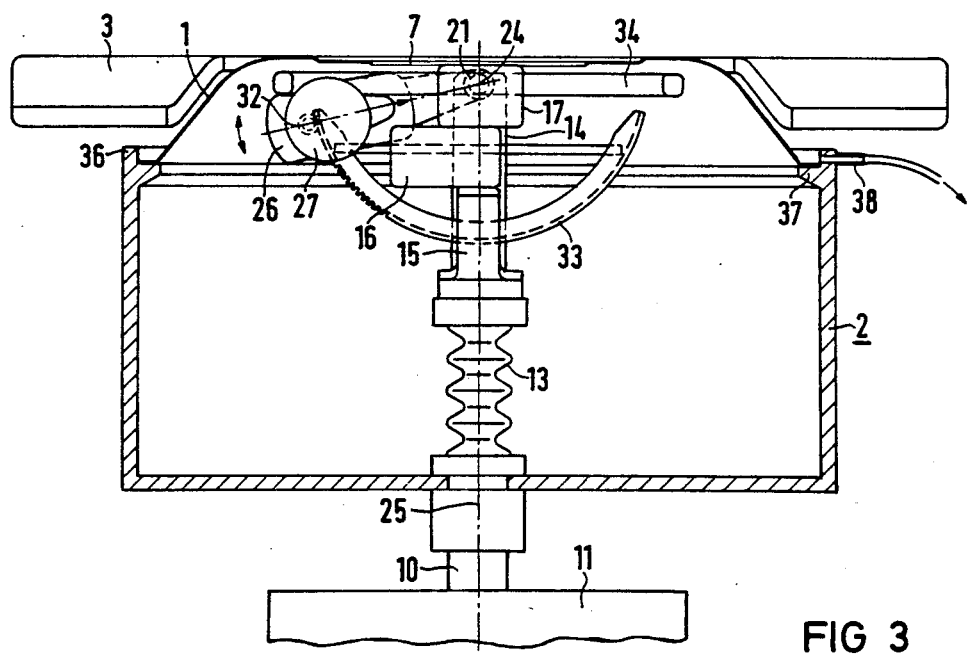
FIG. 3 is a longitudinal cross-section along line III—III of FIG. 1.

In addition to the L-shaped support 26, a semi-circular detector array 34 is attached to the axle extending along horizontal axis 24. This detector array curves around container 17 with the four ultrasonic converters which are held by support 15 in the shape of a quarter circle around the container's symmetrical axis 23. Feed connection 35 which provides for keeping the tank full of fluid, can be seen on bottom 9 of the tank. As shown in FIG. 3, rim 36 of the fluid tank extends several centimeters above seat 37 of cover 1. A run-off connection 38, located in the wall, is provided for the fluid overflowing from central opening 7, in the cover, into the rim area.

Figure 2:
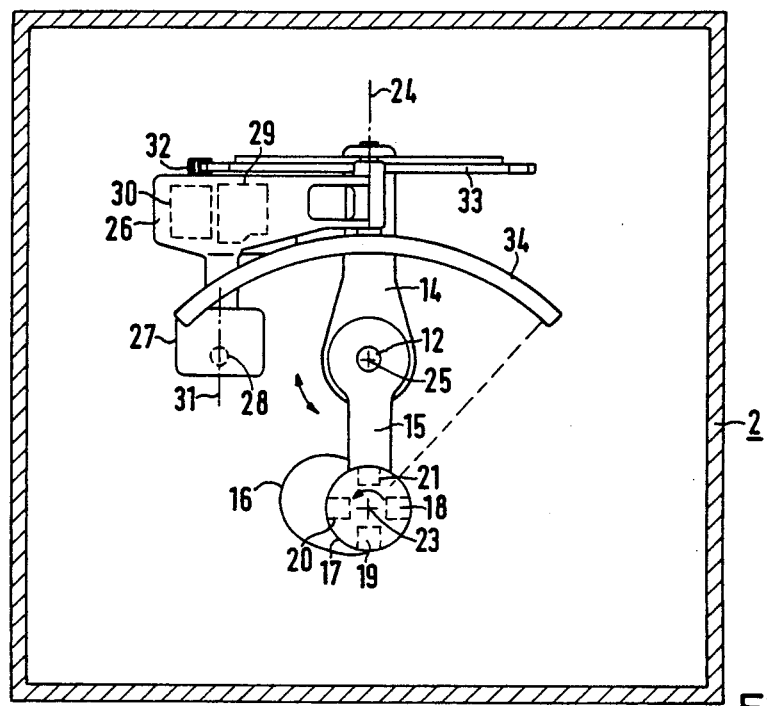
FIG. 2 is a top view of the fluid tank with the cover removed, showing the rotating transmitting and receiving system contained in the tank.

FIG. 2 shows a top view of the elements in fluid tank 2 with cover 1 removed. The two angled supports, 14, 15 are shown opposite each other. FIG. 2 also shows that detector array 34 is curved around symmetrical axis 23 of container 17 in the shape of a quarter circle. In addition, FIG. 2 shows the design of L-shaped support 26 more clearly. This support is designed so that it cannot collide with detector array 34 in either of its two extreme positions during its rotation around horizontal axis 24. FIGS. 2 and 3 illustrate such extreme positions.

In FIG. 3, which shows a cross-section along line III—III of FIG. 1, the shape of semi-circular gear 33 and the position of pinion 32 on L-shaped support 26 can be seen. FIG. 3 also shows the position that detector array 34 must occupy whenever "coronal sections" close to the chest wall are to be recorded. Horizontal axis 24, around which the second transmitting and receiving system for producing "sagittal sections" rotates, is also shown. It can be seen clearly in this Fig. that there is no room for control elements extending above the level of horizontal axis 23 when L-shaped support 26 is rotated.

If an examination is to be made using the ultrasonic tomography device, fluid tank 2 is filled by pumping fluid through feed connection 35 and into the tank. When the fluid tank is completely filled, the excess fluid spills over central opening 7 in cover 1. It then runs along the outside wall of the cover in the channel located on the fluid tank between extending rim 36 of the tank and seat 37 of the cover. The fluid then flows from the channel to a collection basin (not shown) via run-off connection 38.

The female patient 5 can lay down on patient support table 3 so that her breast 8 to be examined hangs down into fluid tank 2 through central opening 7. In doing so, the patient can also rest her head on head support piece 6. When the ultrasonic transmitting system on the left in FIG. 1, is activated, and as container 17 rotates around its symmetrical axis 23, a sound beam is generated in turn by each of the four ultrasonic converters 18, 19, 20 and 21 which are attached to the container. This sound beam spreads horizontally over detector array 34, which is attached to horizontal axis 24 on the opposite side of the object under examination.

Because sound lobes 39, 40 as shown in FIG. 4, occupy a highly concentrated area which increases its distance from the ultrasonic converter 41, 42 as the diameter of the ultrasonic converter increases, highly localized signals, from areas of the object under examination that have different distances from the ultrasonic converter, can be obtained from each of the four ultrasonic converters housed in container 17. Therefore, container 17, with the four attached ultrasonic converters, is not merely rotated to the extent that an ultrasonic converter scans the entire width of the object under examination with its sound lobe; but rather it is rotated approximately 360 degrees around its symmetrical axis, so that each ultrasonic converter repeats the same measurement for each of the different planes. The signals of each respective ultrasonic converter for each plane are evaluated and a horizontal or "coronal section" is shown on the screen of a display unit (not shown) using the evaluated signals.

Shaft 12, which can be shifted along the length of tubular shaft 10, is then lowered so that the two angled supports 14, 15 are positioned a few millimeters lower. In this lower plane, the next "coronal section" is repeated in the manner already described. Several closely-layered parallel "coronal sections", one below the other, can thus be made through the object under examination.

L-shaped support 26 with container 27 and four ultrasonic converters 28 which function according to the reflection method and are arranged around the container perimeter, can be rotated counterclockwise, as shown in FIG. 3, by almost 180 degrees and at a constant speed, irrespective of its function of making "coronal sections". For this purpose, motor 30, which drives pinion 32, is activated. The pinion moves along semicircular gear 33, taking with it L-shaped support 26 and the second ultrasonic transmitting and receiving system. The other motor 29, which is attached to the L-shaped support, is activated simultaneously with motor 30 which drives the pinion. This motor rotates container 27 with the four ultrasonic converters attached to its perimeter around its horizontallly-aligned symmetrical axis 31. The rotation of the container is much faster than the movement of L-shaped support 26 along the outer edge of gear 22. In this way, the object under examination can be bombarded with ultrasonic waves from different directions by the four ultrasonic converters attached to container 27. While the L-shaped support revolves along the outer edge of the gear, a vertical or "sagittal section" can be made through the object under examination. These "sagittal sections" can be made through the object under examination by using drive 11 to turn tubular shaft 10 in the other direction. By reviewing the respective "coronary" and "sagittal sections", three-dimensional statements concerning the pattern of certain objects covered in the two sectional areas can be made, on the one hand, while on the other hand, a distinction can be made between real scanning elements and those caused by artifacts which therefore do not appear in the other corresponding sectional views. Also, "sagittal sections" can be used to make statements concerning those regions close to the chest wall that cannot be reached via "coronal sections".

There has thus been shown and described a novel method and apparatus for an ultrasound tomography device which fulfills all the objects and advantages sought. Many changes, modifications, variations and other uses and applications of the subject invention will, however, become apparent to those skilled in the art after considering this specification and the accompanying drawings which disclose embodiments thereof. All such changes, modifications, variations and other uses and applications which do not depart from the spirit and scope of the invention are deemed to be covered by the invention which is limited only by the claims which follow.

What is claimed is:
1. In an ultrasonic tomography device having
   (a) a first ultrasonic transmitting and receiving system for scanning an object to be examined from different angles line by line,
   (b) a fluid tank for receiving a predetermined quantity of fluid for immersing said object to be examined therein,
   (c) a cover for said fluid tank, said cover having an opening for inserting said object to be examined,
   (d) first support and driving means for rotating said ultrasonic transmitting and receiving system in said fluid tank about a vertical axis which is aligned toward said opening in said cover,
   the improvement comprising:
   (e) a second ultrasonic transmitting and receiving system for reflection tomography,
   (f) means defining a horizontal axis which intersects said vertical axis only a few millimeters below the surface of said predetermined quantity of said fluid,
   (g) second support means having an angled shape, said second support means having attached thereto said horizontal axis defining means,
   (h) second driving means for rotating said second support means about said vertical axis,
   (i) L-shaped third support means revolvingly suspended from said horizontal axis means, said third support means having a free end and supporting said second ultrasonic transmitting and receiving system on said free end, and
   (j) means for revolving said second ultrasonic system through a median perpendicular to said opening in said cover, whereby the direction of radiation of said second ultrasonic system is aigned toward the center of said opening in said cover.

2. The improvement of claim 1, wherein a semi-circular gear surrounding said horizontal axis is secured to said angled second support means, and wherein a motor means is secured to said L-shaped third support means for driving a pinion that engages said gear.

3. The improvement of claim 1, further comprising means for vertically adjusting said first and second support means along said vertical axis.

4. The improvement of claim 3, wherein the transmitting and receiving systems are supported by a shaft which is rotatable and adjustable as to height along the vertical axis.

5. The improvement device of claim 1, wherein the first ultrasonic transmitting and receiving system functions as a transmission tomograph and the associated detector array is attached to the second angled support which rotates around the vertical axis.

6. The improvement of claim 4, wherein the detector array is curved around the first transmitting system in the shape of a quarter circle, and is located in the same horizontal plane as the transmitting axis.

7. The improvement of claim 4, wherein the detector array is attached to an axle extending along the horizontal axis.

8. The improvement of claim 1, wherein the two angled support means are rigidly coupled to each other.

* * * * *